United States Patent
D'Acosta et al.

(10) Patent No.: US 10,899,684 B2
(45) Date of Patent: Jan. 26, 2021

(54) PROCESSES FOR AN IMPROVEMENT TO GASOLINE OCTANE FOR LONG CHAIN PARAFFIN FEED STREAMS

(71) Applicant: Swift Fuels, LLC, West Lafayette, IN (US)

(72) Inventors: Chris D'Acosta, West Lafayette, IN (US); Jeffery Miller, Naperville, IL (US); Robert Hoch, Hensonville, NY (US)

(73) Assignee: SWIFT FUELS, LLC, West Lafayette, IN (US)

( * ) Notice: Subject to any disclaimer, the term of this patent is extended or adjusted under 35 U.S.C. 154(b) by 0 days.

(21) Appl. No.: 16/242,465

(22) Filed: Jan. 8, 2019

(65) Prior Publication Data

US 2019/0210942 A1    Jul. 11, 2019

Related U.S. Application Data

(60) Provisional application No. 62/614,762, filed on Jan. 8, 2018.

(51) Int. Cl.
| | |
|---|---|
| *C07C 4/06* | (2006.01) |
| *C10G 11/05* | (2006.01) |
| *C10G 47/16* | (2006.01) |
| *C10L 1/04* | (2006.01) |
| *C10G 69/04* | (2006.01) |
| *C10G 51/02* | (2006.01) |

(Continued)

(52) U.S. Cl.
CPC .............. *C07C 4/06* (2013.01); *C10G 11/05* (2013.01); *C10G 47/16* (2013.01); *C10G 51/026* (2013.01); *C10G 63/04* (2013.01); *C10G 69/04* (2013.01); *C10L 1/04* (2013.01); *C07C 2529/48* (2013.01); *C10G 2300/1085* (2013.01); *C10G 2300/301* (2013.01); *C10G 2300/305* (2013.01); *C10L 10/10* (2013.01); *C10L 2290/141* (2013.01)

(58) Field of Classification Search
CPC .................................... C07C 5/03; C07C 4/06
USPC ......................... 585/752, 275, 277
See application file for complete search history.

(56) References Cited

U.S. PATENT DOCUMENTS

| | | | |
|---|---|---|---|
| 3,714,023 A | * | 1/1973 | Stine ...................... C10G 59/02 208/62 |
| 4,753,720 A | | 6/1988 | Morrison |

(Continued)

OTHER PUBLICATIONS

International Search Report and Written Opinion in related PCT/US2019/012679 dated May 8, 2019.

(Continued)

*Primary Examiner* — Thuan D Dang
(74) *Attorney, Agent, or Firm* — Woodard, Emhardt, Henry, Reeves & Wagner, LLP

(57) ABSTRACT

Methods for making higher-octane fuel components from a feed stream of C8+ paraffins, including catalytically cracking the C8+ paraffins using a Zeolite catalyst to produce a reaction product of mid-chain paraffins and olefins and short-chain paraffins and olefins. The reaction product comprises liquid phase paraffins having an increased Octane Value over the feed stream paraffins. The reaction product further comprises a gas phase of short-chain paraffins which are separated from the liquid phase. In embodiments, the short chain olefins are hydrogenated to form mid-chain paraffins and a gas phase containing short-chain paraffins.

22 Claims, 8 Drawing Sheets

(51) Int. Cl.
    *C10G 63/04*        (2006.01)
    *C10L 10/10*        (2006.01)

(56)            References Cited

U.S. PATENT DOCUMENTS 4,827,076  A       5/1989   Kokayeff et al.
    5,082,983  A       1/1992   Breckenridge et al.
    5,326,463  A       7/1994   Fletcher et al.
    5,407,559  A  *    4/1995   Degnan ................ C10G 35/095
                                                              208/211

OTHER PUBLICATIONS

Zhao, X. Characterization of Modified Nanoscale ZSM-5 Catalyst and Its Application in FCC Gasoline Upgrading Process, Energy & Fuels, vol. 20 (May 12, 2006) pp. 1388-1391.

* cited by examiner

PROCESSES FOR AN IMPROVEMENT TO GASOLINE OCTANE FOR LONG CHAIN PARAFFIN FEED STREAMS

FIELD

Disclosed is a low-severity, catalytic reaction process applied selectively to long-chain paraffinic compounds, particularly n-paraffins, such as those present in traditional, catalytic reforming processes. The low-severity process, operated with or without hydrogen, converts targeted long-chain paraffins to higher-octane compounds ideal for gasoline blending, along with a byproduct of mixed light gases.

BACKGROUND

Global demand for high-octane gasoline blendstocks continues to grow to support new higher-compression internal combustion engines. The presence of long-chain paraffin compounds ("LCPs"), particularly n-paraffins, in petroleum products output from traditional catalytic reformers, typically lowers the octane value of the aromatic-rich blendstocks produced for the octane pool. These LCP compounds are subsequently blended into the gasoline pool and thereby reduce octane levels, resulting in lower fuel efficiency for spark-ignited combustion engines.

The Octane Value of a gasoline fuel component is an important factor to resist engine knocking in high-compression piston engines. Octane is calculated, for example, as motor octane number (MON) or research octane number (RON). As used herein, the term "Octane Value" is defined as the average (MON+RON)/2.

In a typical petroleum refinery, high-octane gasoline blendstock that is output from the catalytic reforming process, or from fluid catalytic crackers, is sent straight to the gasoline blending pool. However, such units as catalytic reformers may fail to process long-chain paraffins effectively, as that would require operating the reformers under stressful conditions, which can result in heavy volume loss (i.e. 5%-30%), and in many cases excessive coking and/or shortened life of the catalyst. The result is an excess amount of lower-octane, long-chain paraffin in the reformate. The presence of a large portion of these undesirable paraffin constituents—$C_8$ and higher long-chain paraffins—can needlessly lower the octane value of the entire gasoline pool.

Traditional catalytic naphtha reforming is operated at high reactor temperature, ca. 500° C., and pressures up to 340 psi, which favor formation of aromatic gasoline range hydrocarbons. Unlike catalytic reforming, the present invention is operated at lower temperatures and lower pressures, which favor paraffin cracking without aromatic saturation.

Also, in a typical refinery, naphtha-hydrotreating is a precursor to catalytic reforming and is designed to eliminate sulfur that could damage the reformer catalyst. However, naphtha-hydrotreating results in increased paraffin levels. Reformate feed streams therefore typically contain an undesirable amount of low-octane, long-chain paraffins in the C8+ range which are suitable for utilizing this invention.

Transforming long-chain paraffins to high-octane blendstocks is a challenge for the catalytic reformer. To increase octane, catalytic reformers typically must increase operating severity, which results in higher energy costs and lower liquid volume yields. Increasing severity also results in coking and/or shorter catalyst life cycles, particularly impacting semi-regenerative reformers. Refiners are thus challenged to maximize liquid yields, lower costs and sustain catalyst life.

This invention is also unlike traditional gasoil hydrocracking which saturates poly-aromatic compounds and cracks C16 to C44+ paraffin compounds to diesel and jet fuel. Gasoil hydrocracking is operated at high pressures and 300-475° C. and very high pressures (typically 500 to 3000 psi) to favor saturation of poly-aromatic compounds, the removal of sulfur and the cracking of larger high-molecular-weight paraffins. As a result, the gasoil hydrocracking process reduces the aromatic content while creating lighter paraffin compounds in the diesel fuel boiling range. In such a process, significant quantities of aromatics present after gasoil hydrocracking are considered undesirable. Also, gasoil hydrocracking catalysts may contain platinum (Pt) or palladium (Pd), or alternatively Molybdenum (Mo) sulfide promoted by nickel (Ni) or cobalt (Co). Because of the large size of gasoil molecules, larger pore zeolites are generally used in gasoil hydrocracking. Unlike gasoil hydrocracking, this invention uses smaller pore, less harsh zeolite catalysts operating at far lower severity levels resulting in no saturation of aromatic compounds.

Raising the final octane number of gasoline components would add value to the overall gasoline pool. The octane values of heavier paraffin components are generally much lower than those of aromatic compounds in catalytic reforming effluent (reformate), and therefore tend to drag down the overall octane value of reformate by 1 to 10 octane numbers using the ((R+M)/2) method. A key factor in increasing the Octane Value is reducing the proportion of higher-boiling, heavy paraffins, particularly n-paraffins. These higher boiling paraffins impose an octane "Drag Factor" on the gasoline blend. The term "Octane Drag Factor" refers to the comparison of the Octane Value of a given paraffin as compared to the Octane Value of 87. Thus, Octane Drag Factor=Octane Value−87. FIG. 1 presents the Octane Drag Factor for various n-paraffins and iso-paraffins.

Table 1 demonstrates the significance of the average Octane Drag Factor by carbon number for higher-boiling n-paraffins and iso-paraffins typical of reformate samples.

TABLE 1

| Paraffin in Typical Reformate Samples | Boiling Range | Octane (R = M)/2 Drag Factor |
|---|---|---|
| C6 Paraffins | 50-69° C. | −11 |
| C7 Paraffins | 80-99° C. | −23 |
| C8 Paraffins | 99-125° C. | −33 |
| C9 Paraffins | 125-151° C. | −35 |
| C10 Paraffins | 152-183° C. | −57 |
| C11 Paraffins | 183-190° C. | −124 |
| C12 Paraffins | 190-216° C. | −176 |
| C13 Paraffins | 216-235° C. | −178 |

The effect of different n-paraffins on Octane Value by carbon number in a typical refinery LCP product stream is demonstrated in Table 2.

TABLE 2 n-Paraffin Impact on RON and MON
Typical Reformate Feed: n-Paraffin Content

| C# | Compound | Typical Wt % | RON | MON |
|---|---|---|---|---|
| 4 | n-Butane | 0.2 | 113 | 114 |
| 5 | n-Pentane | 1.0 | 62 | 66 |
| 6 | n-Hexane | 2.1 | 19 | 22 |
| 7 | n-Heptane | 10.5 | 0 | 0 |

TABLE 2-continued n-Paraffin Impact on RON and MON
Typical Reformate Feed: n-Paraffin Content

| C# | Compound | Typical Wt % | RON | MON |
|---|---|---|---|---|
| 8 | n-Octane | 6.8 | −18 | −16 |
| 9 | n-Nonane | 2.5 | −18 | −20 |
| 10 | n-Decane | 0.7 | −41 | −38 |
| 11 | n-Undecane | 0.2 | −65 | −64 |
| 12 | n-Dodecane | 0.7 | −88 | −90 |
| 13 | n-Tridecane | 0.1 | −89 | −93 |
| | Total n-Paraffin | 24.8 | — | — |
| | C8+ n-Parafinn | 11.0 | — | — |

As shown in FIG. 2, increasing levels from 0 to 10% of $C_{9+}$ heavy paraffins, particularly n-paraffins, in a reformate stream reduces Octane Values from 104.3 down to 96.2 octane.

This demonstrates that even a small percentage of C8+ long-chain-paraffin constituents, particularly n-paraffins, can substantially hinder octane values in gasoline blendstocks.

SUMMARY

In one aspect, referred to herein generally as Increase to Fuel Economy, or the "I2FE Process", feed containing $C_{8+}$ paraffins is processed to selectively convert low-octane, long-chain paraffins into shorter chain paraffins by chemical reaction, with or without added hydrogen. The I2FE Process provides an increase in the octane level with high energy density compounds of the liquid yield for use as high-octane gasoline blendstocks. The short-chain paraffins reduce the octane drag particularly of n-paraffins impacting the blended Octane Value of the liquid yield. This process also produces a clean byproduct of mixed light $C_1$ to $C_5$ hydrocarbon gases and liquids (upon cooling) for reuse in fuels.

An object of the I2FE Process is to increase the octane of a base feedstock by eliminating low-octane constituents which are transformed to higher value products with minimal yield loss.

Another object of the I2FE Process is to increase the octane rating of gasoline blendstocks. In a particular aspect, it is an object to upgrade the octane performance of petroleum reformate used in blending premium gasoline, while producing a byproduct of sulfur-free $C_{1+}$ light gases.

A further object is to provide a process useful in a refinery, typically downstream of naphtha reforming, to selectively crack long-chain paraffin compounds, particularly n-paraffins while preserving the high-octane aromatic molecules.

The I2FE Process advantageously allows the tailored separation and processing of the reformate by means of slit stream, distillation and/or other separation methods to selectively treat the paraffin compounds having the highest drag factor on the overall Octane Value, thereby increasing the octane value of the effluent with minimal loss.

The process is tailored based upon the characteristics of typical aromatic-rich feed streams with LCP's and the selective targeting of paraffinic compounds to be transformed to high-octane constituents to increase octane and limit volume loss.

DESCRIPTION

Figure 1:
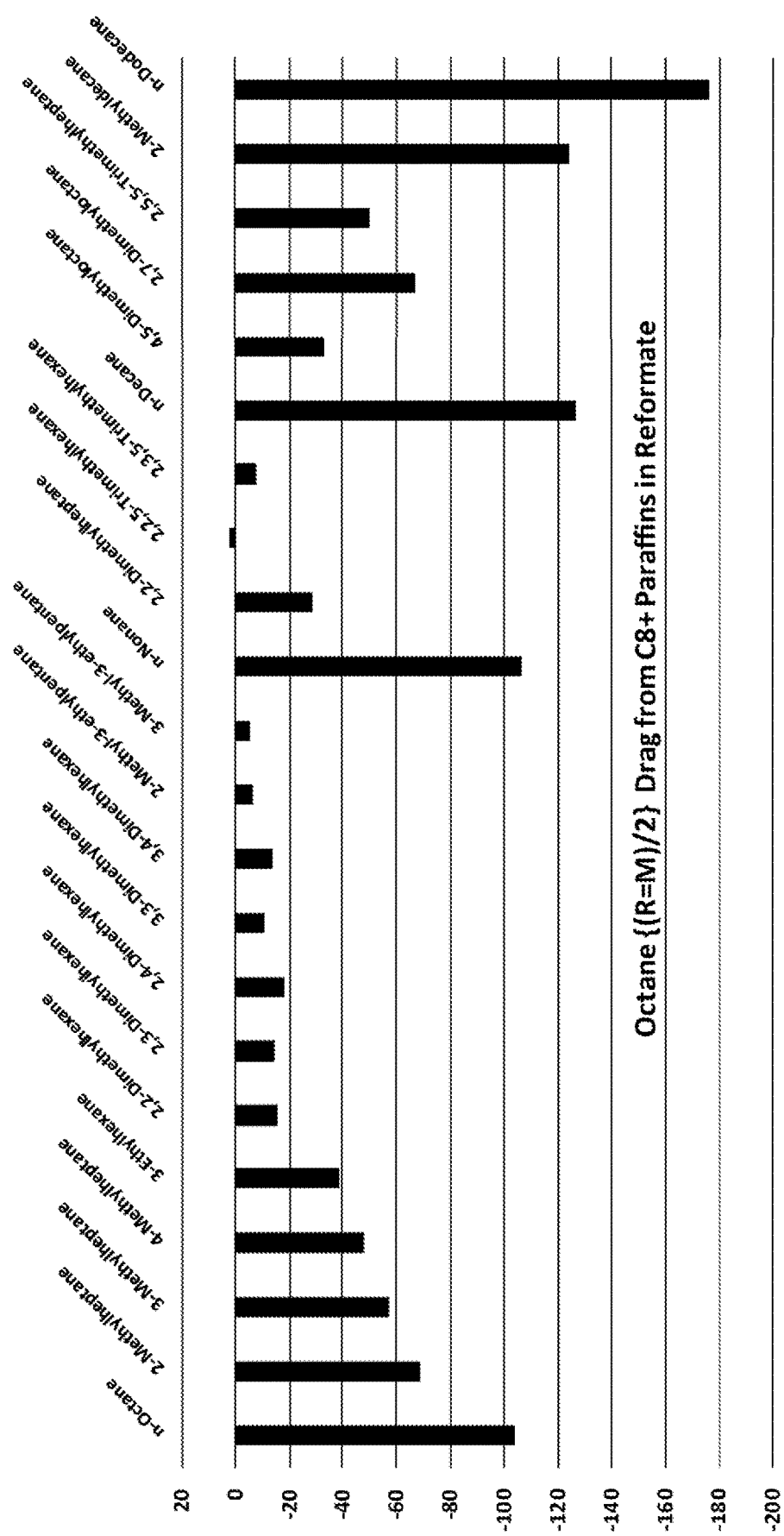
FIG. 1 is a diagram comparing Octane Drag Factor for various C8 to C12 n-paraffins and iso-paraffins typical in reformate.
Figure 2:
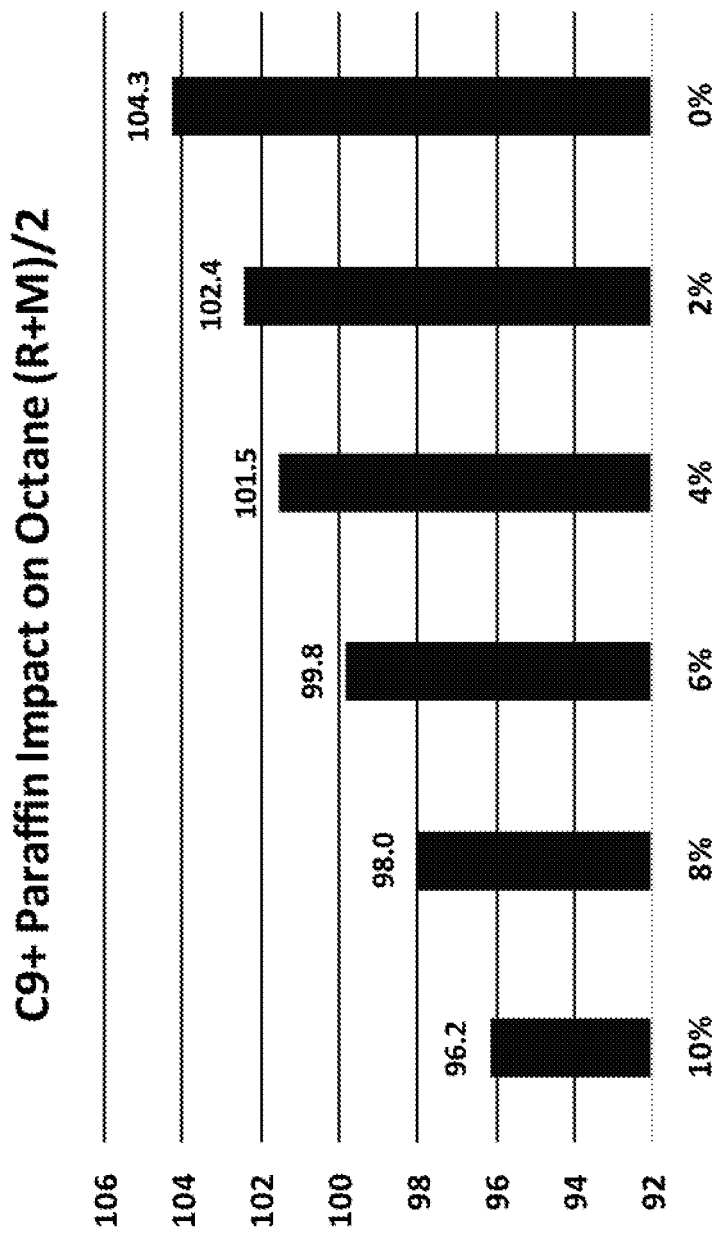
FIG. 2 is a diagram showing the impact of n-Paraffins (% wt.) on reformate Octane Value.

For the purpose of promoting an understanding of the principles of the invention, reference will now be made to the embodiments illustrated herein and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. Embodiments of the invention are shown in detail, but it will be apparent to those skilled in the relevant art that some features that are not relevant to the present invention may not be shown for the sake of clarity.

The I2FE Process is a unique process for the treatment of base feedstock containing higher-boiling paraffins to increase overall Octane Value. The low severity cracking process provides for targeting of long-chain paraffins without a significant effect on other components, e.g., aromatics.

In refining, the I2FE Process differs significantly from catalytic naphtha reforming. The typical catalytic reformer is configured to increase the aromatic content of a naphtha stream by (a) dehydrogenation of cycloalkanes, and (b) cyclization of $C_6+$ alkyl chains followed by dehydrogenation. The cyclization/dehydrogenation step has the slowest rate of reaction, and therefore full conversion of paraffins to aromatics is notably incomplete in reforming. Some broad-spectrum cracking does occur as a result of using harsh reforming catalysts operating at high severity levels, however this can result in undesirable high yield losses (i.e. 5-30%) with no specific impact on the low-octane compounds. Heavy paraffins present in the catalytic reformer effluent (reformate), and in some cat-cracked gasoline, have very low octane, and removal of small amounts of these can significantly increase the octane of the gasoline blendstock.

Overview

The I2FE Processes increase Octane Value by converting long-chain paraffins into shorter chain, higher octane paraffins or a combination of high-octane paraffins and olefins. A primary focus is the treatment of n-paraffins based on the proportion and Octane Values of those components.

As an overall process, the conversion of paraffins may be represented by the following three steps:

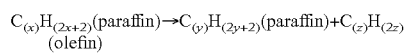

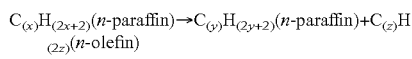

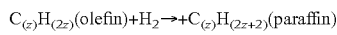

where x=y+z. In the first two steps, the C8+ paraffins, including particularly the n-paraffins are converted into combinations of shorter paraffins (e.g., n-paraffins) and lower carbon olefins (e.g., C5 paraffin+C3 olefin, C6+C2, etc.). In the third step, if hydrogen is present, the lower carbon olefins are hydrogenated to form the corresponding paraffins, e.g., n-paraffins.

The I2FE Process includes the treatment of long-chain paraffins. As used herein, a "long-chain paraffin", or "LCP", is a paraffin containing 8 or more carbons. In an embodiment, the LCPs contain from 8 to 13 carbons, and are referred to herein as C8-13 LCPs. LCPs may include n-paraffins, iso-paraffins and cyclo-paraffins. In another embodiment, the LCPs are non-cyclic, and in another aspect the LCPs are normal, straight-chain n-paraffins having from 8 to 13 carbon atoms. An "LCP Feed" is a feed stream that includes long-chain paraffins. For example, a $C_8$-$C_{13}$ LCP Feed is a feed stream that contains paraffins including 8-13 carbons. In an embodiment, the disclosed processes specifically target the cracking of n-paraffins, namely, n-octane, n-nonane, n-decane, n-undecane, n-dodecane and n-tridecane, as these have the most undesirable octane ratings in the feed (e.g. reformate) that negatively impact the octane value of the gasoline blendstocks.

It will be appreciated that the LCP Feed may include other components. For example, a $C_8$-$C_{13}$ LCP Feed may include many other paraffins, such as 2-methylheptane, an isomer of n-octane, and cyclooctane, a cyclo-paraffin. An LCP Feed may also include other types of hydrocarbons such as aromatics and olefins. In an aspect, the paraffins designated as being in an LCP Feed comprise at least 10 wt % of the LCP Feed, more preferably at least 25 wt %, and most preferably at least 40 wt %. For purposes herein, all percentages are wt % unless indicated otherwise.

By way of example, in the absence of hydrogen, the n-paraffin $C_8H_{18}$ may be converted to $C_6H_{14}$ (hexane) and $C_2H_4$ (ethylene). In an alternative example, the $C_8H_{18}$ may instead be converted to $C_5H_{12}$ (pentane) and $C_3H_6$ (propylene). It is also possible that paraffins formed in the reaction may be subsequently converted to even shorter paraffins and olefins. In the presence of hydrogen and a metal-acid catalyst in these examples, olefins produced from the reaction are largely converted to paraffins.

It will be appreciated that a similar reaction scheme applies for non-normal paraffins, e.g., iso-paraffins. That is, for example, higher carbon iso-paraffins may be converted to lower carbon olefins and paraffins. In the presence of hydrogen and a metal-acid catalyst, the lower carbon olefins are converted to the corresponding paraffins. The Average Octane Value for C8+ non-normal paraffins is ~70 Octane, while the average Octane Value for C8+ n-paraffins is below −20 Octane. Cracking both types of paraffins will make the Octane Value go higher. Thus, while the primary focus of the I2FE process is directed to the conversion of n-paraffins, it will be appreciated that iso-paraffins that are present may be similarly converted.

The disclosed processes selectively transform long-chain paraffins to increase the overall Octane Value of the blendstock. Therefore, in an aspect, disclosure herein of the treatment of the n-paraffins also includes treatment of other paraffins, e.g., iso-paraffins, that are also present. The mid-chain C4-C6 paraffins are of somewhat lesser importance to cracking as they typically have lower volumes with a more acceptable octane rating. In general, the disclosed processes produce a C5+ liquid product with an increased Octane Value over the feed stream to the process. Embodiments may provide increases of Octane Value by at least 1 unit, preferably at least 5 units, above the feed stream Octane Value.

The I2FE Process can be tailored under a wide variety of scenarios to selectively crack long-chain, paraffin compounds, particularly n-paraffins, at low temperatures and low pressures resulting in improved yields of high-octane gasoline blendstocks. The processes can be applied to a wide variety of long-chain, paraffin feeds. For example, the I2FE Process is useful downstream of various existing process streams in a refinery. In preferred embodiments, the I2FE Processes can be effectively applied to output streams downstream of a catalytic reformer (reformate) or a catalytic cracker (cat-cracked gasoline) as a precursor to the gasoline blending process. The composition of the I2FE feed stream determines the spectrum of compounds to be processed, the suitable operating conditions of the process, and the choice of catalyst for the reaction.

As one example, a refinery reformate with 30% total paraffin content (including straight-chain and branched chain paraffins) was transformed in accordance with the present disclosure. As shown in Table 3, the reformate had a 5.5 Octane Value increase with byproducts of clean light hydrocarbon gases:

TABLE 3

| | Octane Increase | | |
|---|---|---|---|
| | RON | MON | (R + M)/2 |
| Reformate Input | 95.8 | 85 | 90.4 |
| Product Effluent | 101.3 | 90.5 | 95.9 |

In another example, a reformate feed having an n-paraffin profile as shown in Table 4 was treated using the I2FE Process. Table 4 shows in the column "Standard I2FE Feed" the n-paraffin content of a reformate feed stream comprising 11.36 wt % n-paraffins in the C4-C12 range. The n-paraffins underwent a variety of changing operating conditions (at 250, 270, 300° C.) and the results show how the n-paraffin compounds were reduced, up to 58 wt %, from the I2FE catalytic reaction. Further, the composition of the n-paraffins showed a substantial shift from C4-C12 to C3-C9 range of compounds.

TABLE 4

| | | Weight % of n-paraffin compounds | | | |
|---|---|---|---|---|---|
| Compound | C# | Standard I2FE Feed | I2FE Effluent (250° C.) | I2FE Effluent (270° C.) | I2FE Effluent (300° C.) | % Delta 300° C. vs. Feed |
| Methane | 1 | 0.00 | 0.00 | 0.00 | 0.00 | — |
| Ethane | 2 | 0.00 | 0.00 | 0.00 | 0.00 | — |
| Propane | 3 | 0.00 | 0.02 | 0.10 | 0.19 | — |
| N-Butane | 4 | 0.20 | 0.10 | 0.33 | 0.49 | 149% |
| N-Pentane | 5 | 0.21 | 0.24 | 0.57 | 0.66 | 214% |
| N-Hexane | 6 | 0.17 | 0.25 | 0.42 | 0.39 | 133% |
| N-Heptane | 7 | 4.78 | 4.33 | 3.43 | 2.11 | −56% |
| N-Octane | 8 | 3.15 | 2.82 | 1.65 | 0.76 | −76% |
| N-Nonane | 9 | 1.92 | 1.40 | 0.42 | 0.13 | −93% |
| N-Decane | 10 | 0.73 | 0.31 | 0.04 | 0.00 | −100% |
| N-Undecane | 11 | 0.16 | 0.00 | 0.00 | 0.00 | −100% |
| N-Dodecane | 12 | 0.03 | 0.01 | 0.02 | 0.01 | −57% |
| TOTAL n-Paraffins | | 11.36 | 9.49 | 6.97 | 4.75 | −58% |

As a result of the I2FE cracking, the n-paraffins were reduced from 11.4 wt % in the feed to 4.8 wt % in the liquid effluent. The iso- and cyclo-paraffins and olefins were reduced by 2 wt %, and the aromatics increased to 67 wt % of the total I2FE liquid effluent, compared to 58 wt % of the reformate feed.

Table 5 depicts the same n-paraffin compounds of Table 4 pre- and post-I2FE reaction but applying the (R+M)/2 Octane Value to demonstrate the octane×weight % index factor that results from the reduction in n-paraffins. As shown in Table 5, the octane×weight % of the n-paraffin range moved from −93 for the feed stream to as high as +89 as a result of the I2FE process. On a weighted average basis, the Octane Value shifted from −8 up to +19, a 27-point increase largely attributable to the reduction in the low-octane, long-chain n-paraffin compounds.

TABLE 5

| | | n-Paraffin Octane × Weight % | | | |
|---|---|---|---|---|---|
| Compound | (R + M)/2 | Pre-I2FE Feed | Post-I2FE 250° C. | Post-I2FE 270° C. | Post-I2FE 300° C. |
| Methane | | | | | |
| Ethane | | | | | |
| Propane | | | | | |
| N-Butane | 114 | 22.4 | 11.8 | 37.7 | 55.7 |
| N-Pentane | 64 | 13.5 | 15.5 | 36.6 | 42.5 |
| N-Hexane | 21 | 3.4 | 5.1 | 8.7 | 7.9 |
| N-Heptane | 0 | 0.0 | 0.0 | 0.0 | 0.0 |
| N-Octane | −17 | −53.6 | −47.9 | −28.0 | −12.9 |
| N-Nonane | −19 | −36.5 | −26.6 | −7.9 | −2.5 |
| N-Decane | −40 | −28.9 | −12.4 | −1.4 | 0.0 |
| N-Undecane | −64 | −10.3 | 0.0 | 0.0 | 0.0 |
| N-Dodecane | −89 | −2.9 | −1.3 | −1.4 | −1.3 |
| Σ (Octane × Wt %) | | −92.9 | −55.7 | 44.2 | 89.4 |
| Σ(Octane× Wt %)/Σ Wt % (Avg) | | −8.2 | −5.9 | 6.4 | 19.6 |

Table 6 depicts the total compositional impact of the I2FE process on the entire reformate feedstream for the above illustration. The I2FE Process was targeted on reducing the low-octane n-paraffin compounds. Side reactions did have a small impact on other aliphatic compounds (iso-paraffins, cycloparaffins and olefins) resulting in a net 1.9% decrease in concentration of these compounds. The aromatic content of the I2FE liquid effluent increased its concentration up to 14%, a highly desirable result since reformate is the primary source of aromatics in gasoline. In total, the Octane Values (using (R+M/2) method) of the I2FE effluent versus the reformate feedstream increased by up to 8.2 in this example. This result is largely attributed to the 58% wt. reduction in higher n-paraffins in the I2FE effluent.

TABLE 6

| Compound Type | Reformate Feed | I2FE Effluent (250° C.) | I2FE Effluent (270° C.) | I2FE Effluent (300° C.) | % Delta 300° C. vs. Feed |
|---|---|---|---|---|---|
| n-Paraffins | 11.36 | 9.49 | 6.97 | 4.75 | −58% |
| Iso-Paraffins | 24.21 | 23.57 | 23.42 | 22.35 | −8% |
| Naphthalenes | 4.02 | 3.84 | 4.20 | 4.44 | 10% |
| Aromatics | 58.34 | 61.13 | 63.52 | 66.77 | 14% |
| Olefins | 1.33 | 0.99 | 1.08 | 0.88 | −34% |
| — | 0.74 | 0.97 | 0.80 | 0.82 | 11% |
| TOTAL | 100.00 | 100.00 | 100.00 | 100.00 | 0% |

I2FE System

Figure 3:
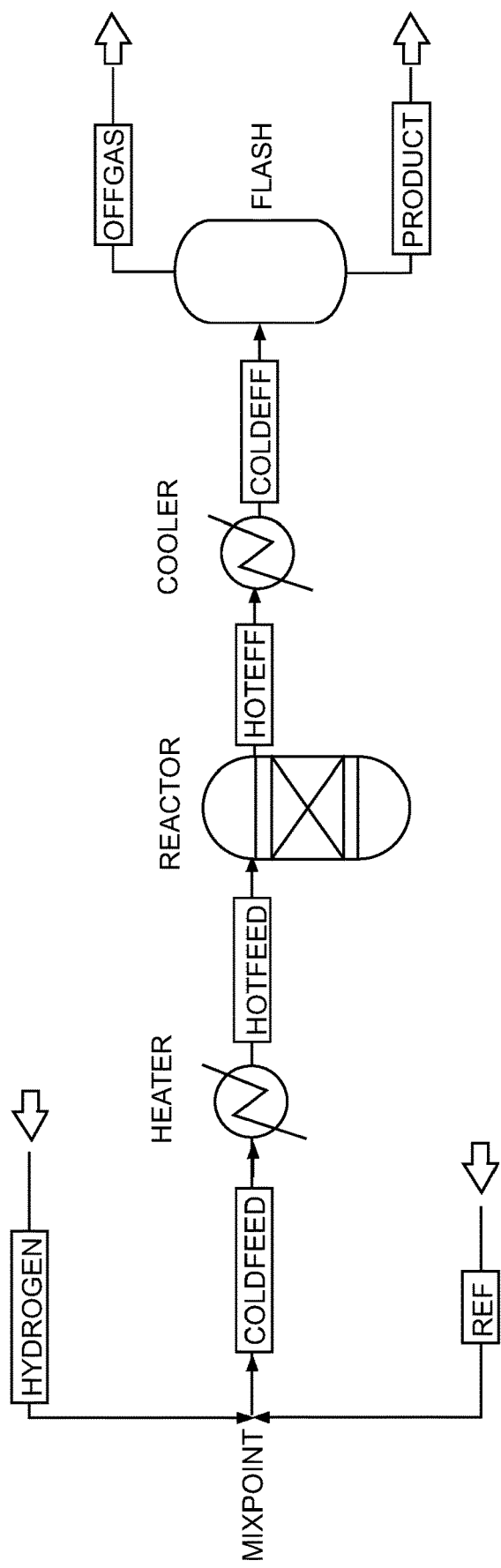
FIG. 3 is a process flow diagram showing a Cracking System process including on-purpose hydrogen.

A study was conducted to exemplify the extent of paraffin cracking and recovery in a simulated system based on real reaction data. A feedstock of 70,000,000 gallons of reformate per year was simulated with a four-unit operation to determine heat exchange and capital cost. The chemical compositions for the reformate feed ("REF") and the outlet of the small-scale reactor were utilized as the input for the refinery simulation. A process flow diagram is shown in FIG. 3 including on-purpose hydrogen.

The reformate feed is combined with the high-pressure hydrogen feed and the resulting cold feed is moved into a preheater for the reactor. The resulting hot feed enters the cracking reactor where the paraffins are cracked over a suitable catalyst, e.g., a zeolite/molybdenum catalyst. The reaction conditions are set at 365° C. and 100 psi with a space velocity of 1.5 WHSV. The hot effluent is then cooled to 35° C. The cold effluent enters an isothermal flash drum and light gases (i.e. $H_2$, paraffins, olefins) are off gassed from the liquid product steam. As an alternative, the cooler could be designed as a preheater for the reactor.

Figure 4:
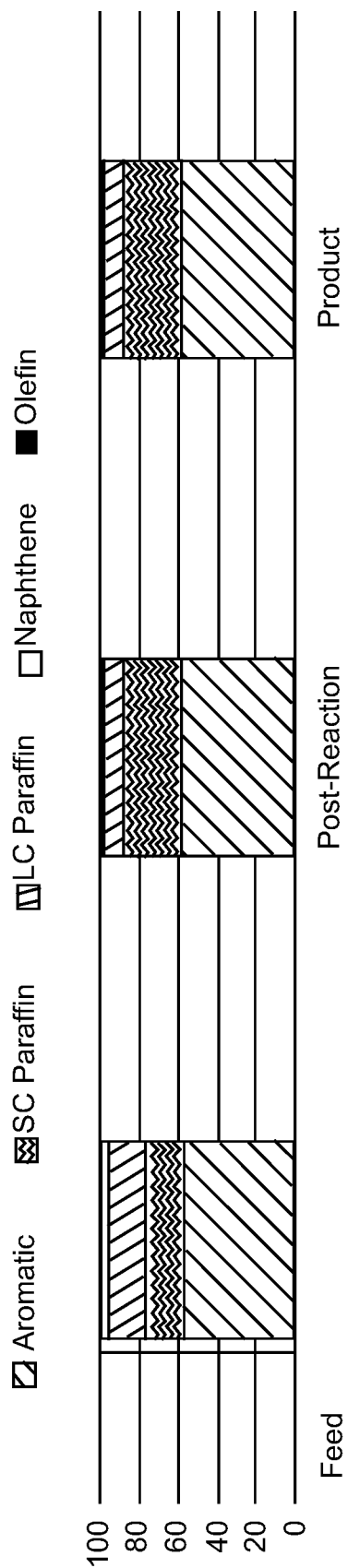
FIG. 4 is a diagram showing compositions of the pre-reaction, post-reaction, and post-flash feed streams.

The compositions of the pre-reaction, post-reaction, and post-flash feed streams are shown in FIG. 4.

The composition notably changes in the Reactor where long-chain n-paraffins are cracked into shorter, higher octane, paraffins. Total paraffin content remains relatively consistent, in part because cracking of paraffins only leads to lighter paraffins. Long-chain paraffin content in the product stream lowers from 19.9% feedstock content to 10.8%, and in turn the middle chain content increases by 27%. The decrease in long-chain paraffin composition only amounts to about a 5% loss in mass after flash distillation. This 5% loss in mass is equivalent to a 2% loss in volume for this system.

Table 7 provides more specific data for this system. As shown, the amount of C7+ paraffins in the product decreased by approximately half the amount of long-chain paraffins in the reformate feed. The middle-chain paraffins increased 27%.

TABLE 7

Simulation Data with On-Purpose Hydrogen

| Lb/hr | REF | HYDROGEN | HOT FEED | HOT EFFLUENT | PRODUCT | OFFGAS |
|---|---|---|---|---|---|---|
| Hydrogen | 0 | 506 | 506 | 6 | 0 | 6 |
| Paraffin | 22455.9 | 0 | 22455.9 | 22918.0 | 20113.2 | 2804.8 |
| Middle Chain Paraffin | 11103.5 | 0 | 11103.5 | 16893.3 | 14166.2 | 2727.1 |
| Long Chain Paraffin (C7+) | 11261.9 | 0 | 11261.9 | 5876.4 | 5828.2 | 48.2 |
| Alkene | 90.5 | 0 | 90.5 | 148.3 | 118.8 | 29.5 |
| Naphthenes | 1267.0 | 0 | 1267.0 | 639.0 | 628.4 | 10.6 |
| Benzene | 1515.9 | 0 | 1515.9 | 2002.5 | 1969.8 | 32.8 |
| Toluene | 7653.1 | 0 | 7653.1 | 8974.4 | 8931.8 | 42.5 |
| Xylenes | 9186.0 | 0 | 9186.0 | 9984.2 | 9970.2 | 14.0 |

TABLE 7-continued

Simulation Data with On-Purpose Hydrogen

| Lb/hr | REF | HYDROGEN | HOT FEED | HOT EFFLUENT | PRODUCT | OFFGAS |
|---|---|---|---|---|---|---|
| Trimethylbenzenes | 3908.6 | 0 | 3908.6 | 4090.7 | 4089.1 | 1.6 |
| Misc. Alkyl Benzenes | 10577.5 | 0 | 10577.5 | 8455.2 | 8450.9 | 4.2 |
| Total | 56563.9 | 506 | 57069.9 | 57069.9 | 54153.4 | 2916.5 |
| GPM | 146 | | | | 142.6 | |

Catalytic Paraffin Cracking

Figure 5:
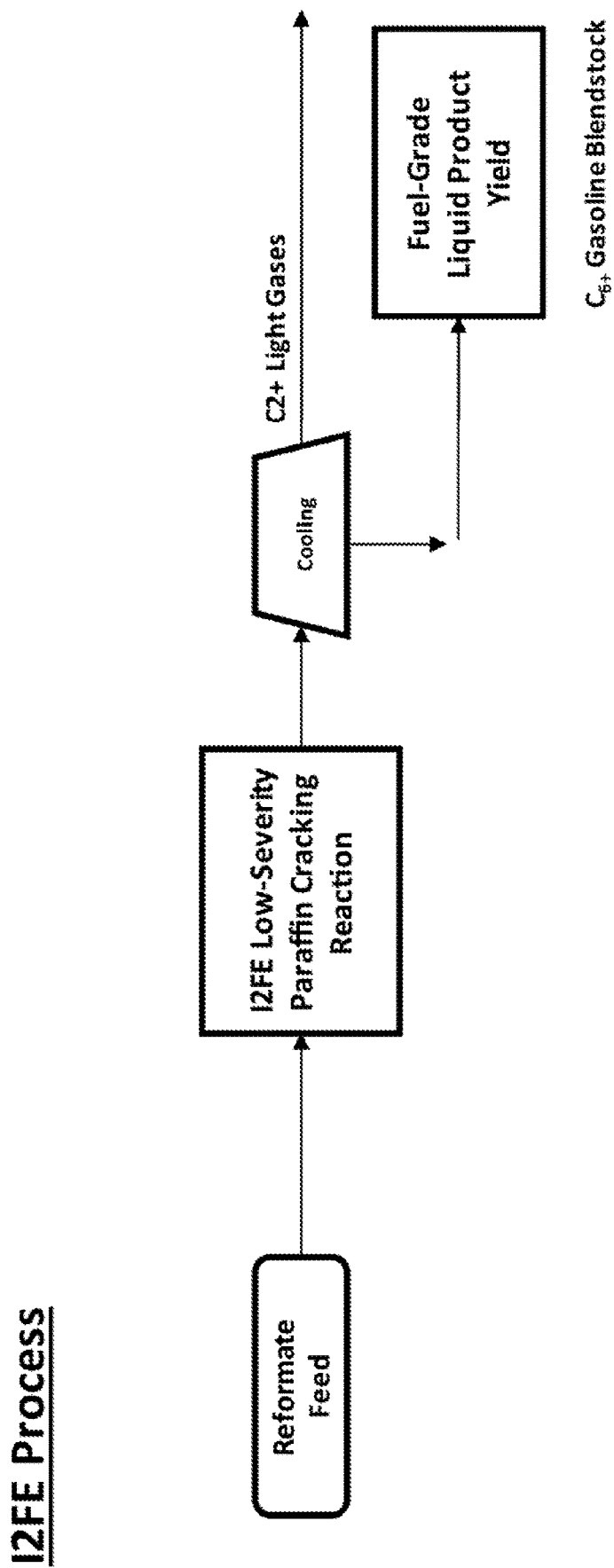
FIG. 5 is a diagram of an I2FE process without hydrogen.

The basic I2FE cracking process proceeds as shown in FIG. 5. The process involves the use of a suitable long-chain paraffin feed ("LCP Feed") to the low-severity, paraffin cracking chamber. The cracking chamber is configured to convert the LCPs preferably to middle-chain paraffins. As used herein, a "middle-chain paraffin", or "MCP", is a paraffin that has 5 to 7 carbon atoms. MCPs are liquid at room temperature and are contained in the liquid product phase. The MCPs have Octane Values that are higher than the LCPs, thus resulting in a paraffin product that collectively has a higher Octane Value than the paraffin components of the LCP Feed.

As a result of the cracking of the LCP there will be an amount of short-chain paraffins formed. As used herein, a "short chain paraffin", or "SCP", is a paraffin having 4 or fewer carbons. These SCPs are gases at room temperature and are contained in the gaseous product phase.

The cracking of the LCPs may also result in the production of other LCPs, which are shorter than the LCPs from which they are derived, but which are not as short as MCPs. For example, $C_{13}$ may be cracked to form $C_5$ n-paraffin (pentane) and $C_8$ n-paraffin. As $C_5$ n-paraffin is an MCP, and $C_8$ n-paraffin is an LCP, they each have an Octane Value that is higher than that of the $C_{13}$ n-paraffin. They also may have more favorable physical properties, such as viscosity, lower freeze point and fewer carbon-forming deposits, as compared to the original LCPs.

As noted, the resulting product mix includes both a liquid phase and a gas phase. The liquid phase comprises a C5+ paraffin mixture including feedstock components and paraffins resulting from the I2FE cracking process. The gas phase comprises n-paraffins having 4 or fewer carbons, as well as potentially hydrogen and other light gases. As described herein, the C5+ paraffin mixture has an Octane Value in excess of that of the feed stream, typically by 5 or more units. The liquid product thereby represents a fuel blending component having an advantageously increased Octane Value. The C4– gases are separated from the liquid phase product and are available for other uses.

The catalytic paraffin cracking reaction has little impact on aromatics in the LCP Feed. The impact of the transformation is the selective conversion of heavier n-paraffin components. The transformed feed stream then undergoes a simple separation process to remove excess hydrogen from the effluent to be recycled. The liquid stream exits the process with an upgraded octane at high yield.

Hydrogen Consumption

The I2FE cracking process consumes an amount of hydrogen if processed with a metal-acid catalyst. The consumption of $H_2$ is sufficiently low that the I2FE Process may, for a given LCP Feed, be converted without supplemental $H_2$.

Each n-paraffin undergoes a series of cracking reactions that result in the formation of two (or more) smaller paraffins and consumes one molecule of hydrogen. For example:

$$C_{10}H_{22}+H_2 \rightarrow C_4H_{10}+C_6H_{14}$$

Therefore, the moles of hydrogen consumed are equivalent to the increase in moles of paraffin.

In a series of experiments, hydrogen consumption rates were calculated for 65,000 pounds of standard reformate. From the GC data gathered, wt % is interpreted as grams compound per 100 grams total. Using the molecular weight of each component, moles/100 g is calculated, which is then converted to moles/kg. For a typical reformate sample this gives a total amount of n-paraffin of 9.138 moles/kg. After reaction at 300° C., the product has a total of 10.129 moles/kg of n-paraffin, an increase of 0.991 mol/kg. This increase is largely due to hydrocracking. Since the increase in moles of hydrocarbon product is equivalent to moles of hydrogen consumed, 0.991 moles H2/kg reformate was consumed. Converting moles of $H_2$ to mass, then everything to pounds, gives a hydrogen consumption rate of 0.002 lb/lb reformate. A feed of 65,000 lb/h would therefore consume 130 lb H2/h.

In one embodiment the LCP Feed does not need to contain on-purpose hydrogen to support cracking in the I2FE Process. While hydrogen may separately be useful to limit catalyst coking, surplus hydrogen may be scarce, so the I2FE process allows added functionality by the use of dual or multi-bed reactors (fixed, moving or fluid beds) operating in a fashion to allow continuous regeneration of the catalyst. A further alternative is the use of a single automatically regenerative catalyst with a single-bed reactor.

On-Purpose Hydrogen

Figure 6:
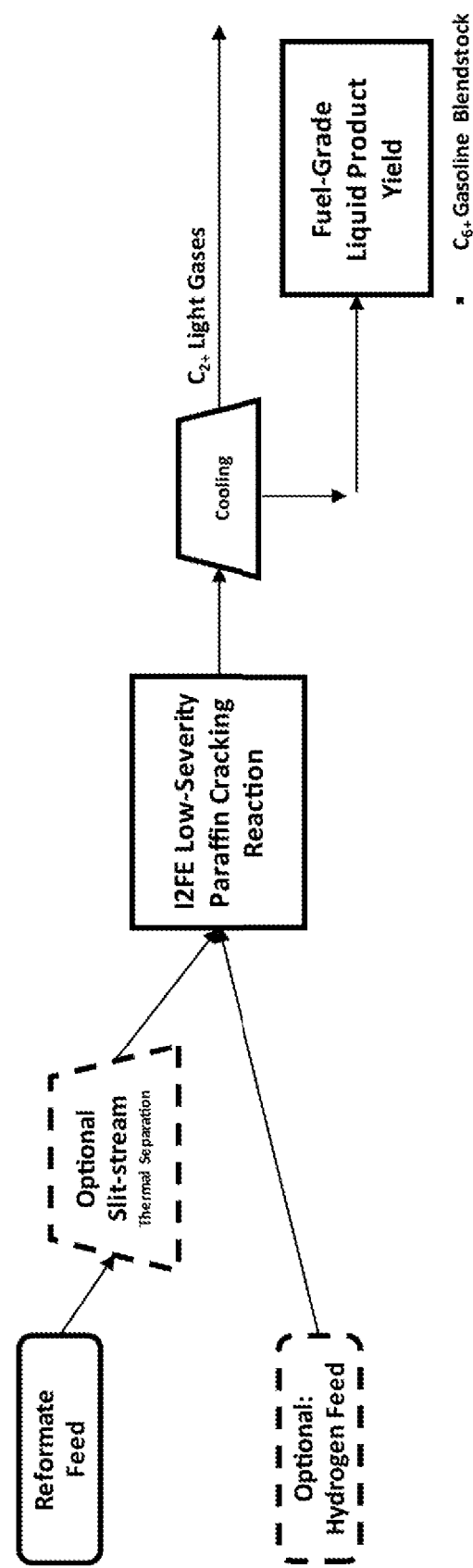
FIG. 6 is a diagram showing a second exemplary I2FE process which includes a hydrogen feed to the cracking chamber.

Referring to FIG. 6, there is shown a second exemplary I2FE Process which includes a hydrogen feed to the cracking chamber. The LCP Feed, e.g., "Reformate Feed", is provided to a reaction chamber where the low-severity paraffin cracking of the long-chain n-paraffins occurs. The supplemental hydrogen feed is available for cracking of the long-chain n-paraffins, and hydrogenation of the alkenes produced during these reactions. The hydrogen feed also contributes to reducing coking of the catalyst and may participate in hydrodealkylation of C2+ alkyl benzenes and hydrogenation of olefins in the feed stream.

Reformate Feed Stream

Petroleum reformate—the liquid effluent of the catalytic reformer—is a gasoline blendstock which can have a wide range of hydrocarbon components depending upon the operating conditions of the reformer. Reformate typically has a significant proportion of long-chain n-paraffins, particularly C8-13 n-paraffins. The presence of the long-chain n-paraffins causes an octane drag on the reformate. The low octane, long chain n-paraffins are the compounds targeted for transformation using the I2FE Process.

The I2FE Processes in a refinery may be desirably positioned downstream of the naphtha reformer. The preferred feedstock for the I2FE Process is a long-chain paraffin effluent from the reformer which has already been desulfurized. Depending on the feedstock source, the reformate feedstock can be processed without other special pre-treatments and can operate with or without on-purpose hydrogen. Some refiners have spare hydrogen available, in which case the use of hydrogen may be preferred as a means to reduce coking of the catalyst, if used in conjunction with a metal-impregnated catalyst. However, operation of the I2FE process without hydrogen does reduce the amount of benzene produced, which is highly advantageous for gasoline blendstocks. The process can operate using the entire effluent reformate stream, using operating conditions to selectively crack the C8+ n-paraffin fractions.

Reformate Compositions

The following Table 8 depicts the typical components of petroleum reformate as exemplified by 5 reformate samples taken from US refineries using the GC method (ASTM D6833). Refineries will have differing results, subject to ever-changing conditions and geography, but this data serves as a range of representative examples.

TABLE 8

Reformate Compositions

| Compounds in Reformate | Weight % | | | | | |
|---|---|---|---|---|---|---|
| | Sample 1 | Sample 2 | Sample 3 | Sample 4 | Sample 5 | AVERAGE |
| Total Paraffins | 42.08 | 15.62 | 30.59 | 24.49 | 29.35 | 28.43 |
| Total Naphthenes | 2.13 | 0.33 | 0.93 | 1.14 | 2.56 | 1.42 |
| Total Olefins | 0.17 | 0.18 | 0.26 | 0.09 | 1.40 | 0.42 |
| Total Aromatics | 55.64 | 83.87 | 68.23 | 74.27 | 66.69 | 69.74 |

These reformate samples had a variety of C6+ n-paraffin compounds as depicted below in Table 9. On average, the very-low-octane n-paraffins (C8 and above) comprised 7 to 14 wt % long-chain n-paraffins, for an average of over 10 wt %.

TABLE 9

C6-C13 n-Paraffin Components

| Compound | Weight % | | | | | |
|---|---|---|---|---|---|---|
| | Sample 1 | Sample 2 | Sample 3 | Sample 4 | Sample 5 | AVERAGE |
| C6 N-Paraffins | 6.34 | 0.00 | 3.88 | 0.00 | 0.10 | 2.06 |
| C7 N-Paraffins | 12.80 | 2.92 | 14.23 | 11.36 | 11.28 | 10.52 |
| C8 N-Paraffins | 6.88 | 6.57 | 5.74 | 7.22 | 7.68 | 6.82 |
| C9 N-Paraffins | 1.95 | 2.84 | 1.18 | 2.76 | 3.68 | 2.48 |
| C10 N-Paraffins | 0.33 | 0.81 | 0.02 | 0.80 | 1.47 | 0.69 |
| C11 N-Paraffins | 0.13 | 0.29 | 0.06 | 0.22 | 0.41 | 0.22 |
| C12 N-Paraffins | 0.83 | 0.64 | 0.34 | 0.64 | 0.84 | 0.66 |
| C13 N-Paraffins | 0.05 | 0.07 | 0.00 | 0.30 | 0.23 | 0.13 |

Reduced Severity Reformate

Reformate is often processed sub-optimally, due to operating constraints within the reformer operation. However, the I2FE Processes can generate more octane-barrels (Octane Value×liquid volume yield) if the severity of the upstream reformer operation is reduced. This impacts the characteristics of the reformate and the target octane requirements for gasoline blending. Lowering the severity of the reformer provides more liquid volume of lower-octane reformate feedstock for the I2FE Process to convert to higher-octane gasoline blendstock.

In one configuration, the catalytic reformer severity is reduced to increase reformate yield of 5% to 15%, with the reformate having a lower Octane Value, but higher paraffin content. This modified reformate composition is then processed using the novel I2FE Processes, resulting in increased overall yields and higher octane than achievable from the current catalytic reformer process alone. This also helps extend the catalyst life of the catalytic reformer (prone to coking at high severity levels) and improve refinery economics for blending high-octane gasoline.

Cat-Cracked Gasoline Feed Stream

As another example of a feed stream, the I2FE Processes are utilized to process Cat-Cracked Gasoline (CCG) containing long-chain paraffins, although effluent from Cat-Cracked Gasoline is less optimal as feedstock depending on the amounts and types of long-chain paraffins present and other considerations. In one embodiment, a variety of cat-cracked-naptha compounds, output from the catalytic cracking operation, are further processed downstream using the methods disclosed herein. A typical cat-cracked feedstock contains the following compounds listed in Table 10 by wt %:

TABLE 10

Sample Cat-Cracked Feed Stream

| Paraffins ≤C7 | 27.8 |
|---|---|
| Paraffins ≥C8 | 16.3 |
| Naphthenes ≤C7 | 5.8 |
| Naphthenes ≥C8 | 3.2 |
| Olefins ≤C7 | 17.7 |
| Olefins ≥C8 | 2.8 |
| Aromatics | 24.8 |
| Unknown | 1.6 |
| TOTAL | 100.0 |

CCG also typically has a higher concentration of olefins (alkenes) and lower amounts of aromatics compared to the catalytic reformer feed. It is preferred to separate the light CCG stream from the heavier C8+ CCG stream which have lower octane values and only use the heavy stream for the I2FE process. This is to avoid harming the octane value of less than C8 olefins. It is an option to hydrotreat the heavy C8+ stream prior to I2FE processing, which would remove sulfur and increase paraffin content somewhat. Any C8+ olefins processed through the I2FE reactor and saturated by the addition of hydrogen, typically produce shorter-chain paraffins. These C8 to C13 olefins are cracked to regain octane from MCP and olefin products and to provide C2, C3 and C4 off-gases as byproducts.

Feedstock Preprocessing

A given feedstock may be processed prior to use in the I2FE processes. As suggested in FIG. 6, the feedstock may first be processed to enhance the feedstock as an LCP Feed. One purpose of such a pretreatment is to have an increased proportion of heavier, low-octane, paraffin constituents in the LCP Feed.

FIG. 6 shows the optional use of thermal separation of the reformate to isolate the long-chain n-paraffins for feed to the I2FE Process. This provides a more limited volume feed stream for processing. The lighter boiling reformate components are already a satisfactory gasoline blendstock.

A specific boiling range can be established based upon target points to maximize the impact of the octane gain based upon the reformate composition. For example, one embodiment may target a reformate cut above 95° C. (i.e., to isolate C7 n-paraffins and higher) while another embodiment may target reformate above 115° C. (i.e., isolating C8 n-paraffins and higher, but excluding any C8 trimethyl-pentanes and all C7 paraffins and lower) with a different yield profile and octane result. Yet another embodiment may target reformate above 140° C. (i.e., to exclude all C8 paraffins and lower). These optional approaches, applicable to any LCP feed stream, reduce the overall volume of the feedstock to be processed by enhancing the proportion of the high-chain n-paraffins in the feed stream.

In another example, a particular light Cat-Cracked Gasoline stream may possess high olefin content and also, for example, 20% of C8 to C13 n-paraffinic constituents. The hard cut to extract only the 20% n-paraffinic portion for cracking reduces the capital and operating costs of the reactor and catalyst, as they would only need to handle 20% vs. 100% of this cat-cracked gasoline feed.

An analysis of any proposed feed stream can be undertaken to determine the ideal cut-point temperature to minimize the production of benzenes. For example, restricting propyl-benzene in the feedstock by selective separation (by limiting constituents <159° C.) prior to the C9+ cracking step can result in substantially lower benzene levels in the effluent when using hydrogen and a metal-acid catalyst with minimal impact on octane.

In the alternative, if the entire reformate stream is to be processed, the reactor operating conditions (e.g., temperature, pressure, space velocity, etc.) can be established in the reforming process to selectively target the decomposition of the heaviest compounds without impacting the lighter paraffin compounds that increase volume loss.

Alkyl-Aromatics

According to another embodiment of the process, other components in the feed stream may be "selected out". These may include certain ethyl-, propyl- or butyl-compounds by thermal slit stream or distillation methods. The presence of methyl-aromatic compounds in the feedstock is unchanged by the I2FE reaction since methyl-benzenes do not dealkylate with hydrogen. However, the presence of isolated ethyl-, propyl-, and/or butyl-benzenes in reaction with hydrogen (in the absence of any methyl-groups) may result in the production of benzene molecules plus the off-gassing of ethane, propane or butane, respectively. Such distillation or slit stream processing can also be used to prevent propyl-benzene from being dealkylated—thereby reducing the creation of benzene in the effluent. The absence of hydrogen in the process will also reduce the creation of benzene in the effluent.

Catalysts

The I2FE Processes disclosed herein utilize catalysts that increase octane and, maximize product yield. The catalysts are highly efficient at cracking long-chain paraffin molecules (particularly C10, C9 and C8 paraffins) without significant degradation during the lifecycle of the catalyst. The catalyst used in the I2FE Process generally contains a strongly acidic zeolite, with a high surface area support, for example, alumina. Additionally, there is a weakly active hydrogenation metal, for example Molybdenum oxide, which saturates cracked olefins without saturation of aromatic compounds. See Table 11.

TABLE 11

Process Options for I2FE Catalysts

| Zeolite Catalyst | I2FE Cracking Reaction | |
|---|---|---|
| | w/ H2 | No H2 |
| w/ Metal | Paraffin production w/ minimal coking[1] | Paraffin production w/ olefins & coking[2] |
| No Metal | Olefin production w/ coking & excess H2 | Olefin production w/ maximum coking[3] |

[1]Addition of metal-impregnated catalyst with H2 saturates cracked olefins without saturation of aromatic compounds
[1]Addition of metal-impregnated catalyst with H2 also reduces coking and simplifies reactor design
[2,3]Multi-bed reactor design option will address coking and eliminate need for on-purpose hydrogen (i.e. H2 not required for the I2FE reaction)

As shown in Table 11, both the use of a metal-impregnated catalyst and the use of on-purpose hydrogen impacts the product yield and the effect on the catalyst. A Zeolite catalyst comprising a metal-impregnated catalyst used in the process in the presence of hydrogen will provide paraffins (without olefins) with minimal coking. Various metals are known to support metal-based hydrogenation, including platinum, palladium, rhenium, ruthenium, nickel, molybdenum, cobalt and copper chromium oxide. A molybdenum-impregnated catalyst is an example of a catalyst that is not overly harsh and therefore is less prone to saturate aromatic molecules. The use of a metal-impregnated catalyst without added hydrogen produces paraffins and olefins, along with some amount of coking.

The use of a catalyst without metal-impregnation, along with added hydrogen, produces paraffins with olefins and with coking and excess hydrogen. A catalyst without-impregnation used without the presence of hydrogen will result in the production of paraffins and olefins with maximum coking, as the coking is not controlled without the metal-impregnated catalyst. The use of multi-stage reactors is another option that can be utilized to minimize coking.

Traditional catalytic naphtha reforming technology uses catalysts that contain platinum (Pt) on chloride alumina, often promoted with either tin (Sn) or rhenium (Re) for better yield and stability, respectively. These reforming catalysts are compositionally very different from the I2FE catalysts.

The I2FE Process uses catalysts which are functional to substantially crack the LCPs in the feed stream, while not significantly affecting other components of value in the feedstream. A catalyst is functional to substantially crack the LCPs if it cracks at least 30 wt % of the LCPs, preferably at least 50 wt %, and more preferably at least 75 wt % of the LCPs.

Other components of value may include certain C7+ aromatics known to be useful gasoline components. C5-7 paraffins in the feedstock are generally acceptable in gasoline blends and they constitute components of value that preferably are not cracked as that may reduce the volume of liquid product. As used herein, the term "component of value" is used to refer to C5-C12 alkanes and alkenes;

C7-C12 aromatics. A component of value is not "significantly affected" if the cracking does not react more than 10 wt % of the component, preferably not more than 5 wt %, and more preferably not more than 2 wt % of the component (s) of value. By way of example, a suitable catalyst for the disclosed processes is one which would crack more than 60 wt % of the C8+ n-paraffins in the feed stream but would not react more than 5 wt % of the C5-7 n-paraffins in the feed stream.

In one embodiment, the I2FE Process is performed using a zeolite catalyst. The acidic sites in zeolite catalyze cracking reactions of C8-13 paraffinic compounds more rapidly than other components. The zeolite may also catalyze other cracking reactions, but more slowly. The reactions can be conducted both with and without metal impregnation. The metal allows hydrogen, if present, to add across olefinic compounds that are produced during the cracking mechanism. Not using a metal increases coking of the reactor since olefins will react to create many different heavy compounds.

In one aspect, the processes use a zeolite catalyst having a pore size of 3 to 8 Angstroms. Exemplary surface areas for the catalyst are 400 to 800 m2/gram. Examples of the zeolite catalysts include Si, Al and O, preferably with an Si:Al ratio of 10 to 300. Zeolite catalysts with properties outside of these limitations may also be useful. The catalyst is preferably selected to substantially catalyze the LCPs while not significantly affecting the other components of value in the feed stream.

In embodiments, the catalyst is Zeolite ZSM-5, Zeolite Beta or Zeolite Mordenite. Impregnation of these catalysts all use the same metal at varying concentrations for activity. Aluminum heptamolybdate is one example of a metal used to impregnate the zeolite catalyst with molybdenum. This creates a bifunctional catalyst that is an acid and metal. Zeolites are characterized via the following ways: pore size—3 to 8 angstroms usually; pore structure—many types; and chemical structure—combination of Si, Al, and O. All have ammonium cations (except one version of mordenite) until impregnation and all have molar Si/Al ratios of 10 to 300.

Zeolite Beta has the following properties: 5.5-7 angstroms pore size, SiO2 to Al2O3 molar ratio (Si/Al) ranging from 20 to 50, intergrowth of polymorph A and B structures, and surface area between 600 and 800 m2/gram.

Zeolite Mordenite has the following properties: 6-7 angstroms pore size, sodium and ammonium nominal cation forms, Si/Al ratio of 10 to 30, and surface area between 400 and 600 m2/gram.

In a particular embodiment, the catalyst is Zeolite ZSM-5. ZSM-5 has the following properties: 5-6 angstroms pore size, pentasil geometry forming 10-ring-hole configuration, Si/Al ratio of 20 to 280, and surface area between 400 and 500 m2/gram. Various impregnations can and have been conducted between 1% and 2% molybdenum. ZSM-5 has the ability to preserve chemical composition of the aromatic compounds in the reformate feedstock by minimizing transalkyation. The reaction can be conducted both with and without metal impregnation. The metal allows hydrogen to add across olefinic compounds that are produced during the cracking mechanism. Not using a metal increases coking of the reactor since olefins will react to create many different heavy compounds. The smaller pore size of the ZSM-5 catalyst resulted in far less cracking and transalkylation of aromatic compounds, which are a key part of the reformate stream. The long-chain n-paraffin compounds reacted more favorably to the ZSM-5 structure without disturbing the aromatic compounds.

Zeolite Catalyst Example

Figure 7:
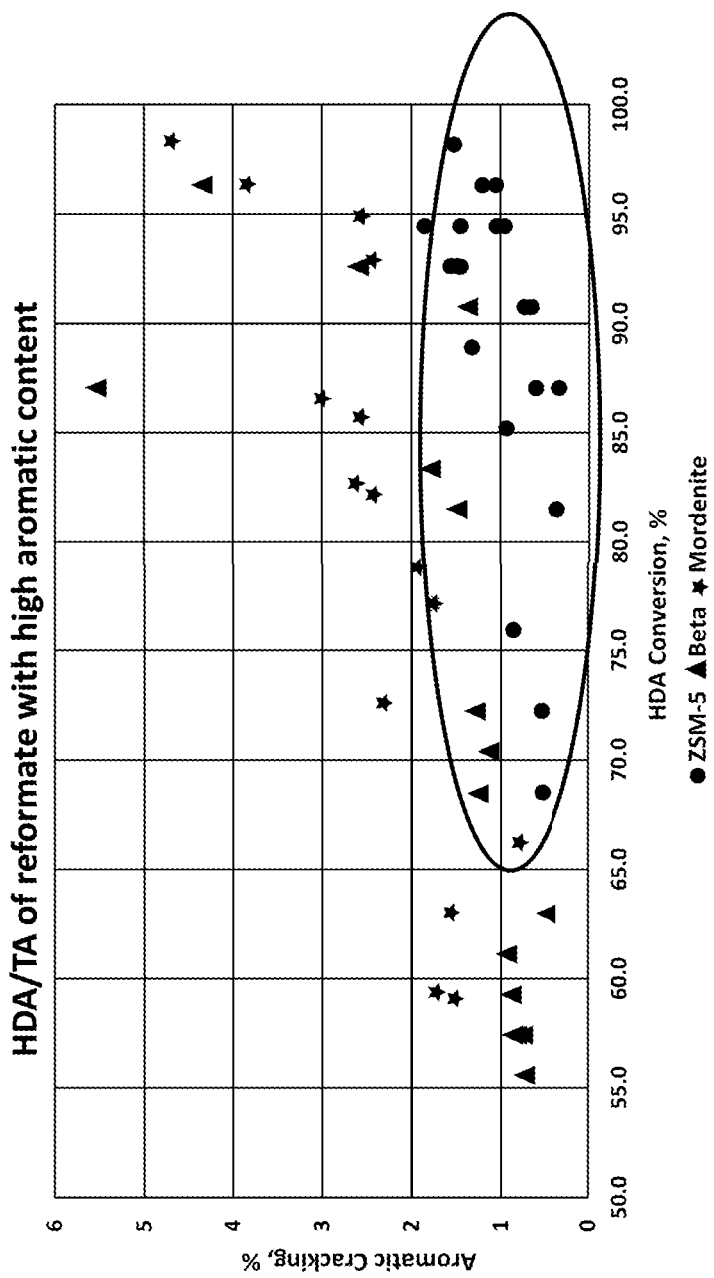
FIG. 7 is a graph showing that aromatics in the feed stream were preserved to a substantial extent using the ZSM-5 catalyst.

In one embodiment, this invention processed an entire reformate stream using a zeolite ZSM-5 catalyst using (1-2% molybdenum) with an operating temperature of 250° C., a pressure of 100 psi, and a WHSV from 1.5 to 3.0. Long-chain paraffins (C8+) with low-octane values were selectively targeted by the tailored operating conditions and were transformed to higher octane constituents for gasoline blending and hydrogen recovery. As shown in Table 12 and FIG. 7, the aromatics in the feed stream were preserved to a substantial extent using the ZSM-5 catalyst.

TABLE 12

| ZSM-5 Preserved Aromatics vs. Beta and Mordenite (% Wt) | | | |
|---|---|---|---|
| | ZSM-5, 1% Mo | Beta, 1% Mo | Mordenite, 1% Mo |
| 1.5 WHSV, h$^{-1}$ | 71.24 | 45.58 | 43.62 |
| 3.0 WHSV, h$^{-2}$ | 80.14 | 61.11 | 62.85 |

As shown below in Table 13, the LCPs with low octane were reduced by 31% and the C5-C7 and lower paraffins (with improved octane, e.g. isopentane, isobutane, etc.) increased by 24%. Heavier olefins and naphthenes were also reduced. Overall, the Octane Value increased 6%, the (pre-blending) benzene level was below 1%, and net volume loss was 5%.

TABLE 13

| | Wt % | | |
|---|---|---|---|
| Key Compounds | Reformate | Reactor Effluent | Delta (%) |
| Paraffins ≤C7 | 16.59 | 20.61 | 24.2% |
| Paraffins ≥C8 | 13.54 | 9.3 | −31.3% |
| Naphthenes ≤C7 | 1.48 | 1.49 | 0.7% |
| Naphthenes ≥C8 | 0.62 | 0.57 | −8.1% |
| Olefins ≤C7 | 0.59 | 0.43 | −27.1% |
| Olefins ≥C8 | 0.45 | 0.12 | −73.3% |
| Aromatics | 66.52 | 66.89 | 0.6% |

Contaminates

The cat-cracked liquid effluent may contain contaminates which call for specialized treatment methods and/or conditions. For example, the C8 to C13 streams of CCG often contain a proportion of sulfur compared to their neighboring C6 to C7 liquid streams, typically up to 100+ ppm. In one embodiment, the I2FE Process applied to the CCG feed uses a metal catalyst compatible to effectively treat and remove sulfur (50 ppm) while also hydrocracking the long-chain n-paraffins. The choice of catalysts for processing CCG requires sensitivity to treating the sulfur without damaging the catalyst.

If processing streams containing sulfur, this invention uses similar zeolite catalysts with a different hydrogenation metal, typically Cobalt-Molybdenum Sulfide, which saturates cracked olefins without saturation of aromatic compounds, while producing hydrogen sulfide (H2S) for extraction. The preferred embodiments of this reaction utilize a Zeolite catalyst (Beta, Zsm-5, Mordenite, Y-zeolite-Faujasite) with Molybdenum-Sulfide or Cobalt-Molybdenum-Sulfide with alumina as a binder support. This catalyst hydrocracks the paraffins and creates H2S, thereby largely removing sulfur from the effluent stream which can then be subsequently blended into the gasoline stream. The embodiment thus combines the hydrotreating (to eliminate sulfur) with hydrocracking in a single step to selectively eliminate the formation of paraffins that tend to have lower octane levels.

The result is an enhanced hydrocarbon stream with a higher-octane value and much lower sulfur content with minimum yield loss for improved gasoline blending. This is distinctly different than traditional hydrotreating methods as it is focused solely on production of high-octane, low-sulfur gasoline blendstocks. This is unique and extremely valuable to the gasoline blending business.

Operating Conditions

The use of the selective I2FE Processes requires the operating conditions to be at uncharacteristically low temperatures and pressures for hydrocracking, to thereby selectively crack the targeted molecules, e.g., C8-13 n-paraffins. This enhances the impact to increase the octane level of the hydrocarbon stream.

Operating conditions for the preferred embodiment of the gas-phase hydrocracking reaction are temperatures ranging from the bubble point of the feed stream up to 370° C., pressure of 50-250 psi, and weight hourly space velocity (WHSV) of 0.5 to 10. Select scenarios may call for conditions that vary from these amounts.

Products

Fuel Blendstocks

The result of the cracking reactions is a higher-octane C5+ liquid phase and a gas phase. The liquid phase effluent typically has a higher yield at lower severity levels than its upstream feed source. It has higher octane values due to the reduction of the octane drag from cracking low-octane, long-chain paraffins into liquid and gas constituents. In one embodiment, the severity level of the upstream catalytic reformer unit is reduced to result in higher liquid yields, offering the process to be utilized to crack a larger portion of long-chain paraffins at a lower cost due to its lower operating temperature and pressure of the process. These liquid hydrocarbon compounds may be used directly in the gasoline blending process.

Typically, gasoline blending in a refinery is the complex integration of as many as 5 to 15 processing streams into the gasoline blending center. These streams may include for example, cat-cracked gasoline (primarily olefins), reformate (primarily aromatics, paraffins), alkylate (iso-paraffins), C4/C5 Isomerate (used for RVP), straight run gasoline (light naphtha), and various specialized distillation cuts to improve fuel performance properties.

The goal of I2FE is to enhance the octane performance of the reformate stream by reducing the n-paraffin content while preserving the aromatic content. Therefore, the product of I2FE is in range of high-octane gasoline components, as an enhanced reformate blendstock, primarily comprised of aromatics, branched and cyclo-paraffins and some olefins all ranging from C4 to C13. Due to the blending and regulatory complexity of light C4 and C5 compounds used for increasing vapor pressure of the final gasoline, it is often desirable to reduce the amount C4 and/or C5 present in the I2FE effluent, as these paraffins and iso-paraffins are typically added at the time of final fuel blending.

Light Gases

The gas phase compounds may be handled in various ways. In one embodiment, the gas phase compounds are rerouted for industrial fuel use or are recycled (including hydrogen) to an upstream process unit (e.g., catalytic reformer). In one embodiment, some C5 and C6 straight chain compounds are subsequently isomerized using existing refinery technology and are used for gasoline RVP blending requirements.

Diesel Fuel

Controlling Benzenes

Benzene content is limited in gasoline blendstocks. Since there are gasoline specifications which set limits on its use, it becomes important to manage benzene levels in the effluent or have a separate benzene offtake for petrochemical use. One feature of this invention is the ability for the process to limit the amount of benzene in the processed effluent using selective separation methods.

Table 14 provides a listing of various alkyl-aromatics. In the absence of methyl groups, such alkyl-aromatics could react with hydrogen to yield benzene.

TABLE 14

| Alkyl-Aromatics | | |
|---|---|---|
| Aromatic Compund | Formula | Boiling Point ° C. |
| ETHYLBENZENE | C8H10 | 136.2 |
| P-XYLENE | C8H10 | 138.4 |
| M-XYLENE | C8H10 | 139.1 |
| O-XYLENE | C8H10 | 144.4 |
| ISOPROPYLBENZENE | C9H12 | 152.4 |
| N-PROPYLBENZENE | C9H12 | 159.2 |
| M-ETHYLTOLUENE | C9H12 | 161.3 |
| P-ETHYLTOLUENE | C9H12 | 162.0 |
| 1,3,5-TRIMETHYLBENZENE | C9H12 | 164.7 |
| O-ETHYLTOLUENE | C9H12 | 165.2 |
| TERT-BUTYLBENZENE | C10H14 | 169.1 |
| 1,2,4-TRIMETHYLBENZENE | C9H12 | 169.4 |
| ISOBUTYLBENZENE | C10H14 | 172.8 |
| SEC-BUTYLBENZENE | C10H14 | 173.3 |
| M-CYMENE | C10H14 | 175.1 |
| 1,2,3-TRIMETHYLBENZENE | C9H12 | 176.1 |
| P-CYNENE | C10H14 | 177.1 |
| O-CYMENE | C10H14 | 178.2 |
| M-DIETHYLBENZENE | C10H14 | 181.1 |
| 1-METHYL-3-N-PROPYLBENZENE | C10H14 | 182.0 |
| N-BUTYLBENZENE | C10H14 | 183.3 |
| 1-METMYL-4-N-PROPYLBENZENE | C10H14 | 183.4 |
| O-DIETHYLBENZENE | C10H14 | 183.4 |
| 1,3-DIMETHYL-5-ETHYLBENZENE | C10H14 | 183.6 |
| P-DIETHYLBENZENE | C10H14 | 183.8 |
| 1-METHYL-2-N-PROPYLBENZENE | C10H14 | 184.9 |
| 1,4-DIMETHYL-2-ETHYLBENZENE | C10H14 | 186.8 |
| 1,3-DIMETHYL-4-ETHYLBENZENE | C10H14 | 188.2 |
| 1,2-DIMETHYL-4-ETHYLBENZENE | C10H14 | 189.5 |
| 1,3-DIMETHYL-2-ETHYLBENZENE | C10H14 | 190.1 |
| 1,2-DIMETHYL-3-ETHYLBENZENE | C10H14 | 193.9 |
| 1,2,4,5-TETRAMETHYLBENZENE | C10H14 | 196.8 |
| 1,2,3,5-TETRAMETHYLBENZENE | C10H14 | 198.0 |

Operating Conditions

Figure 8:
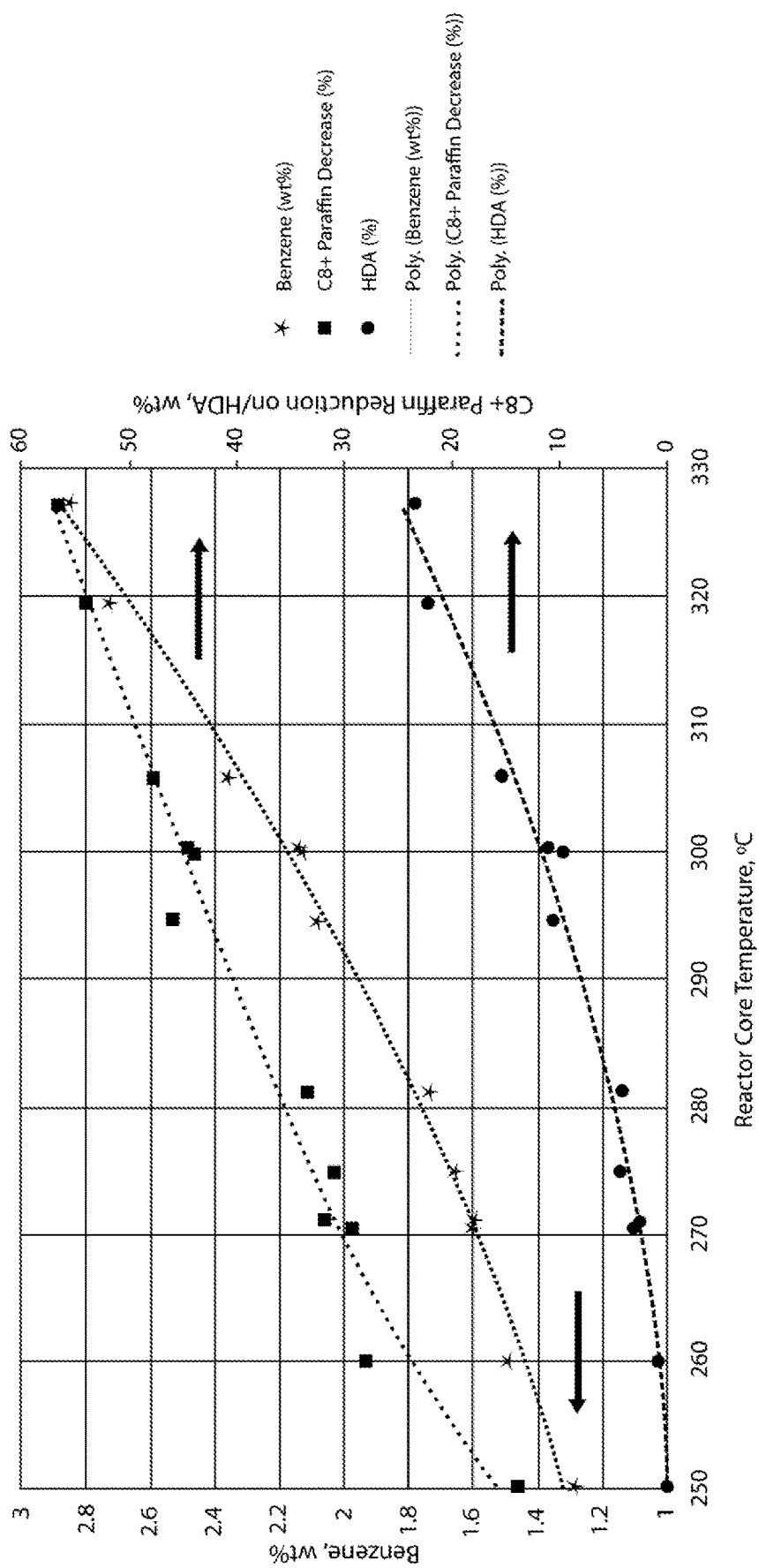
FIG. 8 is a graph showing benzene reduction in comparison to I2FE reactor temperature.

In another aspect, the I2FE operating conditions can be varied in such a way as to selectively minimize any production of benzene (without thermal separation as a precursor) by altering the process temperature, pressure and WHSV to ideal conditions for minimizing benzene. FIG. 8 shows the benzene reduction in comparison to I2FE reactor temperature.

In embodiments, various processing steps may be combined to reduce the production of benzene. For example, selective thermal separations combined with specialized operating conditions can work together to minimize the production of benzene.

In some cases, a benzene thermal separation step may be cost-effective in preparing benzene for downstream BTX operations. In a related embodiment, separating C6-C9 alkyl-aromatics and conducting a hydrodealkylation processing step can further prepare BTX compounds for such petrochemical processing. Hydrodealkylation can eliminate undesirable close boiling aromatic compounds and streamline the BTX petrochemical pre-treatment process. In other cases, the absence of hydrogen in the I2FE process can restrict the conversion of alky-aromatics to benzene, thereby optimizing the process to yield high octane gasoline blendstocks with controlled amounts of benzene, yet below regulatory levels for the final blended gasoline.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected.

The invention claimed is:

1. A method for making a higher-octane fuel component from a feed stream containing C8+ paraffins, comprising:
    catalytically cracking C8+ paraffins in the feed stream using a metal impregnated Zeolite catalyst under operating conditions converting C8+ paraffins in the feed stream to first middle-chain paraffins, first short-chain paraffins, C5-7 olefins, and C4-olefins converted from the C8+ paraffins,
    the C5-7 olefins and the C4-olefins being hydrogenated in the presence of the metal-impregnated Zeolite catalyst to form second short-chain paraffins and second middle-chain paraffins, respectively,
    the reaction product comprising a liquid phase containing first and second middle-chain paraffins and a gas phase containing first and second short-chain paraffins;
    the liquid phase paraffins having an Octane Value that is at least 1 Octane Value higher than the Octane Value of the paraffins in the feed stream; and
    separating the liquid phase from the gas phase.

2. The method of claim 1 in which the metal-impregnated zeolite catalyst is a hydrogenation-metal-impregnated catalyst converting the olefins to paraffins.

3. The method of claim 1 in which the liquid phase further comprises C8+ paraffins.

4. The method of claim 3 and which further includes using the liquid phase as a fuel component.

5. The method of claim 4 in which the feed stream includes C5-13 n-paraffins, the method further comprising separating out a portion of the C5-13 n-paraffins for use as a fuel component.

6. The method of claim 1 in which the catalytic cracking is performed under operating conditions including a temperature below 370° C., a pressure below 250 psig, and a flow rate of 1.5 to about 3 WHSV.

7. The method of claim 6 in which the C8+ paraffins comprise C8-13 paraffins.

8. The method of claim 7 in which the C8+ paraffins comprise C8-13 n-paraffins.

9. The method of claim 8 in which the catalytic cracking is performed under operating conditions to substantially crack the C8-13 n-paraffins.

10. The method of claim 9 in which the feed stream further includes aromatic hydrocarbons.

11. The method of claim 10 in which the feed stream includes aromatics and the catalytic cracking is performed under operating conditions in which less than 5% of the aromatics are saturated.

12. The method of claim 6 in which the feed stream comprises an output stream downstream of a catalytic reformer or a catalytic cracker.

13. The method of claim 12 in which the feed stream comprises a complete reformate stream.

14. The method of claim 12 which further includes addition of hydrogen to the feed stream prior to the catalytic cracking.

15. The method of claim 14 in which the metal-impregnated zeolite catalyst is a hydrogenation-metal-impregnated catalyst converting the olefins to paraffins.

16. The method of claim 12 in which the catalytic cracking is performed without hydrogen other than that present in the output stream to reduce conversion of alkyl-aromatics to benzene and/or reduce coking.

17. The method of claim 12 which further comprises pretreating the feed stream prior to catalytic cracking, the pretreating being selected from the group consisting of thermal separation, slit stream, distillation and sulfur-reduction.

18. The method of claim 17 in which the pretreating is selected from the group consisting of thermal separation to provide a feed stream cut above 95° C., thermal separation to provide a feed stream cut above 115° C., thermal separation to provide a feedstream cut above 140° C., and thermal separation to provide a feedstream cut above 159° C.

19. A method for making a higher-octane fuel component from a feed stream containing C8+ paraffins, comprising:
    catalytically cracking C8+ paraffins in the feed stream using a metal-impregnated Zeolite catalyst operating under conditions converting C8+ paraffins in the feed stream to a reaction product comprising middle-chain paraffins and short-chain paraffins converted from the C8+ paraffins, the C8+ paraffins being converted in a two-step process,
    the C8+ paraffins first being converted to a combination of first short-chain paraffins and first middle-chain paraffins and C4-olefins and C5-7 olefins,
    the C4- and C5-7 olefins being hydrogenated in the presence of the metal-impregnated Zeolite catalyst to form second short-chain paraffins and second middle-chain paraffins,
    the reaction product comprising a liquid phase effluent containing the first and second middle-chain paraffins and a gas phase effluent containing the first and second short-chain paraffins;
    the liquid phase effluent having an Octane Value that is at least 1 Octane Value higher than the Octane Value of the feed stream; and
    separating the liquid phase effluent from the gas phase effluent.

20. The method of claim 19 in which the Octane Value of the liquid phase effluent is at least 3 more than the Octane Value of the feed stream.

21. The method of claim 20 which further includes addition of hydrogen to the feed stream prior to the catalytic cracking.

22. The method of claim 21 in which the C8+ paraffins comprise C8-13 n-paraffins, and the catalytic cracking is performed under conditions to substantially crack the C8-13 n-paraffins.

* * * * *